(12) United States Patent
Frey et al.

(10) Patent No.: US 11,529,147 B2
(45) Date of Patent: Dec. 20, 2022

(54) DRILLING DEPTH AND CONTROL APPARATUS AND METHODS FOR USING THE SAME

(71) Applicant: Mighty Oak Medical, Inc., Englewood, CO (US)

(72) Inventors: George Frey, Englewood, CO (US); Caleb Voelkel, West Glover, VT (US); Adam Jensen, Golden, CO (US); Sean Starkman, Centennial, CO (US)

(73) Assignee: Mighty Oak Medical, Inc., Englewood, CO (US)

( * ) Notice: Subject to any disclaimer, the term of this patent is extended or adjusted under 35 U.S.C. 154(b) by 0 days.

(21) Appl. No.: 17/156,330

(22) Filed: Jan. 22, 2021

(65) Prior Publication Data
US 2022/0039808 A1    Feb. 10, 2022

Related U.S. Application Data
(60) Provisional application No. 62/706,296, filed on Aug. 7, 2020.

(51) Int. Cl.
*A61B 17/16* (2006.01)
*A61B 17/17* (2006.01)

(52) U.S. Cl.
CPC ...... *A61B 17/1626* (2013.01); *A61B 17/1633* (2013.01); *A61B 17/17* (2013.01)

(58) Field of Classification Search
CPC . A61B 17/16; A61B 17/1613; A61B 17/1615; A61B 17/1617; A61B 17/162; A61B 17/1622; A61B 17/1624; A61B 17/1626; A61B 17/1628; A61B 17/1631; A61B 17/1633; A61B 17/17
See application file for complete search history.

(56) References Cited

U.S. PATENT DOCUMENTS

| | | | |
|---|---|---|---|
| 3,486,505 A | 12/1969 | Morrison | |
| 4,039,266 A * | 8/1977 | O'Connell | B23B 49/005 408/202 |
| 4,710,075 A * | 12/1987 | Davison | A61B 17/16 33/512 |
| D329,496 S | 9/1992 | Wotton | |
| 5,480,387 A | 1/1996 | Gabriel | |
| 5,810,828 A | 9/1998 | Lightman et al. | |

(Continued)

FOREIGN PATENT DOCUMENTS

| | | | |
|---|---|---|---|
| AU | 2013251305 B2 | 1/2018 | |
| WO | 2012061733 A1 | 5/2012 | |

(Continued)

*Primary Examiner* — Eric S Gibson
(74) *Attorney, Agent, or Firm* — FisherBroyles LLP; Ian R. Walsworth (57) ABSTRACT

This disclosure relates to drill guides and depth control apparatus for use with a variety of customized or standardized surgical instruments. In embodiments, the apparatus comprises at least a body portion and a collar portion, one or more of which are configured to be coupled to a cutting instrument, such as a drill bit, in a specified location and manner to prevent unwanted movement. In embodiments, the assembly of the body and collar portions may be incrementally adjusted to alter the desired depth of the cutting instrument. Methods for using the foregoing apparatus are also disclosed herein.

19 Claims, 10 Drawing Sheets

(56) References Cited

U.S. PATENT DOCUMENTS

| | | | |
|---|---|---|---|
| 5,895,389 A | 4/1999 | Schenk et al. | |
| 6,231,276 B1 | 5/2001 | Müller et al. | |
| 6,368,325 B1 | 4/2002 | McKinley et al. | |
| 6,951,562 B2* | 10/2005 | Zwirnmann | A61B 17/1655 606/80 |
| 7,048,477 B2* | 5/2006 | Abrams | A61B 17/1617 408/1 R |
| 7,163,542 B2 | 1/2007 | Ryan | |
| 7,210,881 B2 | 5/2007 | Greenberg | |
| 7,261,499 B2 | 8/2007 | Mathis et al. | |
| 7,569,058 B2* | 8/2009 | Zwirnmann | A61B 17/1655 606/80 |
| 7,658,610 B2 | 2/2010 | Knopp | |
| D616,095 S | 5/2010 | Kim | |
| D625,805 S | 10/2010 | Hereford | |
| D627,461 S | 11/2010 | Cantu | |
| 7,844,356 B2 | 11/2010 | Matov et al. | |
| 7,957,824 B2 | 6/2011 | Boronvinskih et al. | |
| D649,638 S | 11/2011 | Habegger | |
| 8,647,032 B2 | 2/2014 | Nordlin et al. | |
| 8,758,357 B2 | 6/2014 | Frey | |
| 8,834,417 B2 | 9/2014 | Moos et al. | |
| 8,870,889 B2 | 10/2014 | Frey | |
| 8,876,444 B1* | 11/2014 | Chanturidze | B23B 51/104 408/191 |
| D719,594 S | 12/2014 | Leugers | |
| D723,896 S | 3/2015 | Durfee | |
| D727,985 S | 4/2015 | Leugers | |
| D732,364 S | 6/2015 | Rinaldis | |
| 9,198,678 B2 | 12/2015 | Frey et al. | |
| 9,289,219 B2 | 3/2016 | Kumar | |
| 9,505,063 B2 | 11/2016 | Santamarina et al. | |
| 9,642,633 B2 | 5/2017 | Frey et al. | |
| D793,831 S | 8/2017 | Russell | |
| D793,832 S | 8/2017 | Russell | |
| 9,801,641 B2* | 10/2017 | Keiser | A61B 17/17 |
| D806,147 S | 12/2017 | Inkster | |
| 10,172,630 B2 | 1/2019 | Ponzer | |
| 10,314,598 B2 | 6/2019 | Knape et al. | |
| 10,327,805 B2 | 6/2019 | Hibner et al. | |
| D868,966 S | 12/2019 | Jamison | |
| D893,027 S | 8/2020 | Peters | |
| 10,758,250 B2* | 9/2020 | McGinley | A61B 17/1622 |
| 11,045,212 B2* | 6/2021 | Pacaccio | A61B 17/8625 |
| 11,154,308 B2* | 10/2021 | Khosla | A61B 90/03 |
| 2004/0265082 A1* | 12/2004 | Abrams | A61B 17/1617 408/226 |
| 2005/0119663 A1 | 6/2005 | Keyer et al. | |
| 2005/0222571 A1 | 10/2005 | Ryan | |
| 2006/0004372 A1* | 1/2006 | Zwirnmann | A61B 17/1633 606/80 |
| 2006/0264955 A1 | 11/2006 | Abdelgany | |
| 2007/0270875 A1 | 11/2007 | Bacher et al. | |
| 2008/0114370 A1 | 5/2008 | Schoenefeld | |
| 2008/0161817 A1 | 7/2008 | Parsons | |
| 2008/0167653 A1 | 7/2008 | Watlington | |
| 2008/0177200 A1* | 7/2008 | Ikehara | A61B 10/025 600/567 |
| 2009/0087276 A1 | 4/2009 | Rose | |
| 2009/0138020 A1 | 5/2009 | Park et al. | |
| 2010/0058603 A1 | 3/2010 | Hoffman | |
| 2010/0217336 A1 | 8/2010 | Crawford et al. | |
| 2011/0238070 A1* | 9/2011 | Santangelo | A61B 17/1635 606/80 |
| 2012/0065590 A1 | 3/2012 | Bierman | |
| 2012/0123417 A1 | 5/2012 | Smith | |
| 2013/0084540 A1* | 4/2013 | Yoshihara | A61C 1/084 433/75 |
| 2014/0155905 A1* | 6/2014 | Keiser | A61B 17/17 606/96 |
| 2014/0276880 A1* | 9/2014 | Li | A61B 17/17 606/96 |
| 2016/0128704 A1* | 5/2016 | McGinley | A61B 17/1626 606/80 |
| 2017/0303940 A1 | 10/2017 | Sperry et al. | |
| 2018/0042619 A1 | 2/2018 | Frey et al. | |
| 2018/0064426 A1 | 3/2018 | Clements et al. | |
| 2018/0140378 A1 | 5/2018 | Ebrahimi | |
| 2018/0153563 A1 | 6/2018 | Kuun | |
| 2018/0161124 A1* | 6/2018 | Huwais | A61B 90/03 |
| 2018/0325528 A1* | 11/2018 | Windolf | A61B 17/1615 |
| 2019/0038385 A1* | 2/2019 | Burke | A61C 8/0089 |
| 2019/0269469 A1* | 9/2019 | Bush, Jr. | A61B 34/20 |
| 2019/0290299 A1* | 9/2019 | Pacaccio | A61B 17/1617 |
| 2020/0138519 A1 | 5/2020 | Frey et al. | |
| 2021/0045754 A1* | 2/2021 | Khosla | A61B 17/1633 |
| 2021/0077788 A1 | 3/2021 | Lesch | |
| 2022/0031364 A1 | 2/2022 | Frey et al. | |

FOREIGN PATENT DOCUMENTS

| | | |
|---|---|---|
| WO | 2014066332 A1 | 5/2014 |
| WO | 2017151335 A1 | 9/2017 |

* cited by examiner

DRILLING DEPTH AND CONTROL APPARATUS AND METHODS FOR USING THE SAME

CROSS REFERENCE TO RELATED APPLICATIONS

This application claims the benefit of and priority to U.S. Provisional Patent Application No. 62/706,296 filed on Aug. 7, 2020 pursuant to 35 U.S.C. § 119(e), which is incorporated by reference herein in its entirety.

FIELD

The present disclosure relates to the field of medical devices generally. More specifically, the present disclosure relates to cutting apparatus and depth control apparatus for use with a variety of customized or standardized surgical instruments. Methods for using the foregoing apparatus and devices also disclosed herein.

BACKGROUND

Many prior art devices used to achieve various drilling tasks or related activities suffer from significant disadvantages, such as poor stability and/or accuracy, difficulty in handling and operating in confined spaces, poor visibility, multiple components that require timely assembly/disassembly and inventory management, and other disadvantages. For example, many drilling apparatus have fast moving parts, rotating parts and/or vibrating parts which prevent the drilling apparatus to be secured in a comfortable and fixed position while in use or which significantly impair the visibility and operation of the operable end of the apparatus. Furthermore, prior art drilling apparatus have little or no depth control or accuracy measures with respect to over-drilling or under-drilling, as the application may tend to require. As an example, during drilling, much of the prior art may cause the drill to plunge deeper into the patient if the depth control apparatus becomes unsecure or unlocks. These problems and shortcomings are even more noticeable when considering prior art drills for use in surgical settings or which otherwise require a high degree of precision.

In addition to the shortcomings with drilling apparatus, fixation devices can also suffer from various shortcomings. For example, pedicle and other types of surgical screws are subject to relatively high failure rates, which is often attributed to a failure of the bone-screw interface. Screws for use in surgical settings may also be limited for use in only certain boney anatomies, specific bone densities, specific trajectories, or with only certain types of drilling apparatus. To address these and other shortcomings, many surgeons use patient-specific apparatus to assist with surgical procedures, in part to ensure accuracy and in part to address the many variables and inherent differences in anatomical features from one patient to the next. U.S. patent application Ser. No. 16/831,215 is incorporated by reference herein for the purpose of describing patient-specific apparatus used in surgical settings.

Accordingly, there is a need for an apparatus that improves the accuracy and efficacy of surgical instruments, such as drilling instruments, enhances depth control and stability when performing drilling operations, and which otherwise overcomes the disadvantages of the prior art. In particular, there is a need for an apparatus that may be safely, securely and selectively attached to an instrument prior to a drilling operation, for example, and which may be customized or preconfigured to the particular patient anatomy to be operated on for safe depth control.

There is also a strong need for an apparatus that improves patient safety during drilling or cutting procedures, in part by controlling the amount of boney purchase during certain surgical procedures requiring the use of drilling or cutting apparatus. For example, in posterior open spinal procedures it is advantageous to control the depth of drilling to the extent where a small anterior breach is achieved in the Sacrum in order to obtain stronger bi-cortical purchase at the sacral promontory. In other areas, an anterior breach is quite dangerous and controlling the depth of a cutting apparatus to prevent a breach may also be advantageous.

The prior art also fails to teach a system for creating a suite of surgical apparatus based on the data set derived from a patient's MRI or CT scan. For example, the availability of patient-specific data (for example, a vertebral body) may allow a surgeon to accommodate for subtle variations in the position and orientation of an instrument, such as a drill bit or screw, to avoid particular boney anatomy, or irregularities in the positioning and alignment of the adjoining vertebral bodies. As another example, the use of patient data may also assist a surgeon in selecting a desired trajectory or depth of an implantable device so as to avoid, for example, crossing the pedicle wall and violating the spinal canal during a spine-related procedure. The use of patient-specific data permits the surgeon to avoid these types of mistakes by creating and utilizing customized apparatus, which may comprise specific end-stops/hard stops, or other safety related features to avoid over-torque or over-insertion of an associated device. This data also permits the surgeon to create a patient-specific apparatus that are oriented to match one or more of the anatomical features derived from the data set, and thereby quickly and efficiently locate and place devices with corresponding patient-contacting surface(s) in the appropriate location and orientation.

It would therefore be advantageous to provide apparatus suitable for use with a surgical procedure that is adapted and/or configured and/or capable of conforming to a plurality of anatomical features of a particular patient, and/or to one or more additional apparatus to assist the surgeon in completing the surgical procedure(s) safely and efficiently, and that otherwise significantly reduces, if not eliminates, the problems and risks noted above. Other advantages over the prior art will become known upon review of the Summary and Detailed Description.

SUMMARY

Embodiments of the present disclosure provide systems, methods, and devices for enhancing surgical procedures, such as drilling operations, including but not limited to in a surgical setting. The embodiments disclosed herein further relate to guides for use with the drilling apparatus described in various embodiments, as well as for use with other apparatus.

In embodiments, the apparatus is for use with a customized or standardized instrument, such as a drill. The instrument preferably comprises a housing or body, a drill bit, which preferably extends out from the drill body, and has a length suitable for use in an open or minimally invasive surgical procedure. In embodiments, the drill bit has a male/female groove or channel along its length, which is beneficial for engaging one or more apparatus described in detail below.

In one aspect, the apparatus may be configured to selectively engage with a drill bit and provide a hard stop for preventing travel of the drill bit beyond a predetermined depth. In one aspect, the apparatus may be easily removed and placed in another location for subsequent procedures requiring a different depth.

In one aspect, the apparatus comprises a body portion and a collar portion, which may be joined together and secured relative to each other and to the drill bit in a locked or unlocked position. In embodiments, the locked and unlocked positions are visible from indicia placed on one or more of the body portion and the collar portion.

In another aspect, the apparatus comprises only a body portion and functions in a similar way as the embodiment comprising a collar portion. In yet another aspect, the apparatus does not comprise a locking feature.

In another aspect, the apparatus is placed along a helical channel on an instrument, such as a drill bit. The helical channel is oriented in the opposite or reverse direction as the cutting blades or edges on the drill bit, which in conjunction with the apparatus prevents the drill bit from over-penetrating if the apparatus becomes loose from the drill bit during use. In preferred embodiments, the apparatus may be selectively configured relative to a desired location along the length of a cutting or drilling bit, and locked to prevent the drill bit from extending through a guide (or other device allowing movement of the cutting or drilling bit but not the apparatus) beyond the placement and configuration permitted by the securing of the apparatus on the cutting or drilling bit. In this configuration, once the drill bit reaches the pre-determined depth, the drill will stop and not proceed further, thereby preventing over-travel. In other embodiments, the helical channel is oriented in the same direction as the cutting blades or edges on the cutting instrument.

In another aspect, the apparatus comprises a viewing window or viewport for reading indicia along the cutting instrument, such as the depth in a desired dimension.

In yet another aspect, the cutting instrument channel comprises a plurality of detents, which interface with a corresponding surface, herein referred to as "ball", on the tab of the body portion. The detents are preferably shaped in a congruent manner to the ball, which allow the apparatus to be secured to the shaft of the cutting instrument.

In one aspect the ball is a spherical shape. In other aspects the ball is rectangular, trapezoidal, cylindrical, etc.

In yet another aspect, the apparatus is permitted to rotate and thereby translate longitudinally along the shaft of the cutting instrument between detents such that a specific rotation of the apparatus equates to an increase (or decrease, if rotated in the opposite direction) of a specified distance. For example, according to one embodiment of the present disclosure, a ¼ turn (i.e., 90° rotation) of the apparatus relative to the shaft of the cutting instrument may move the apparatus by 2 mm, thereby increasing or decreasing the allowable depth of the cutting instrument depending on the direction of rotation.

The apparatus may be used with patient-specific guides or standard guides. Pre-determined depths may be determined, for example, by using CAD software, 3-dimensional models, or in certain embodiments from CT, CTA, MRI, and PET scans or x-rays of a particular patient.

Incorporated by reference in their entireties are the following U.S. patents and patent applications directed generally to methods and apparatus related to surgical procedures, thus providing written description support for various aspects of the present disclosure. The U.S. patents and pending applications incorporated by reference are as follows: U.S. Pat. Nos. 7,957,824, 7,844,356, 7,658,610, 6,830,570, 6,368,325, 3,486,505 and U.S. Pat. Pub. Nos. 2018/0042619, 2010/0217336, 2009/0138020, 2009/0087276, 2008/0161817, 2008/0114370, and 2007/0270875.

Additionally, U.S. Pat. Nos. 8,758,357, 8,870,889, 9,198,678 and 9,642,633 are incorporated by reference for the express purpose of illustrating systems and methods for creating a surgical or cutting guide, such as the ones described herein, using additive manufacturing or other techniques, wherein the device incorporates one or more patient-matched surfaces or is otherwise customized to a particular patient.

The phrases "at least one," "one or more," and "and/or," as used herein, are open-ended expressions that are both conjunctive and disjunctive in operation. For example, each of the expressions "at least one of A, B and C," "at least one of A, B, or C," "one or more of A, B, and C," "one or more of A, B, or C," and "A, B, and/or C" means A alone, B alone, C alone, A and B together, A and C together, B and C together, or A, B and C together.

Unless otherwise indicated, all numbers expressing quantities, dimensions, conditions, and so forth used in the specification and claims are to be understood as being approximations which may be modified in all instances as required for a particular application of the novel apparatus described herein.

The term "a" or "an" entity, as used herein, refers to one or more of that entity. As such, the terms "a" (or "an"), "one or more" and "at least one" can be used interchangeably herein.

The use of "including," "comprising," or "having" and variations thereof herein is meant to encompass the items listed thereafter and equivalents thereof as well as additional items. Accordingly, the terms "including," "comprising," or "having" and variations thereof can be used interchangeably herein.

It shall be understood that the term "means" as used herein shall be given its broadest possible interpretation in accordance with 35 U.S.C., Section 112(f). Accordingly, a claim incorporating the term "means" shall cover all structures, materials, or acts set forth herein, and all of the equivalents thereof. Further, the structures, materials, or acts and the equivalents thereof shall include all those described in the Summary, Brief Description of the Drawings, Detailed Description, Abstract, and Claims themselves.

The Summary is neither intended, nor should it be construed, as being representative of the full extent and scope of the present disclosure. Moreover, references made herein to "the present disclosure" or aspects thereof should be understood to mean certain embodiments of the present disclosure and should not necessarily be construed as limiting all embodiments to a particular description. The present disclosure is set forth in various levels of detail in the Summary as well as in the attached drawings and the Detailed Description, and no limitation as to the scope of the present disclosure is intended by either the inclusion or non-inclusion of elements or components when describing certain embodiments herein. Additional aspects of the present disclosure will become more readily apparent from the Detailed Description, particularly when taken together with the drawings.

The above-described benefits, embodiments, and/or characterizations are not necessarily complete or exhaustive, and in particular, as to the patentable subject matter disclosed herein. Other benefits, embodiments, and/or characterizations of the present disclosure are possible utilizing, alone or in combination, as set forth above and/or described in the accompanying figures and/or in the description herein below.

BRIEF DESCRIPTION OF THE DRAWINGS

The accompanying drawings, which are incorporated herein and constitute a part of the specification, illustrate embodiments of the disclosure, and together with the Summary and the Detailed Description serve to explain the principles of these embodiments. In certain instances, details that are not necessary for an understanding of the disclosure or that render other details difficult to perceive may have been omitted. It should be understood, of course, that the present disclosure is not necessarily limited to the particular embodiments illustrated herein. Additionally, it should be understood that the drawings are not necessarily to scale. In the drawings.

Similar components and/or features may have the same reference number. Components of the same type may be distinguished by a letter following the reference number. If only the reference number is used, the description is applicable to any one of the similar components having the same reference number.

DETAILED DESCRIPTION

The present disclosure has significant benefits across a broad spectrum of endeavors. It is the Applicant's intent that this specification and subsequent claims be accorded a breadth in keeping with the scope and spirit of the disclosure and various embodiments disclosed, despite what might appear to be limiting language imposed by specific examples disclosed in the specifications. To acquaint persons skilled in the pertinent arts most closely related to the present disclosure, preferred and/or exemplary embodiments are described in detail without attempting to describe all of the various forms and modifications in which the novel apparatus, devices, systems and methods might be embodied. As such, the embodiments described herein are illustrative, and as will become apparent to those skilled in the arts, may be modified in numerous ways within the spirit of the disclosure.

By way of providing additional background, context, and to further satisfy the written description requirements of 35 U.S.C. § 112, the following are incorporated by reference in their entireties for the express purpose of explaining and further describing the various tools and other apparatus commonly associated therewith surgical procedures: U.S. Pat. No. 6,309,395 to Smith et al.; U.S. Pat. No. 6,142,998 to Smith et al.; U.S. Pat. No. 7,014,640 to Kemppanien et al.; U.S. Pat. No. 7,406,775 to Funk, et al.; U.S. Pat. No. 7,387,643 to Michelson; U.S. Pat. No. 7,341,590 to Ferree; U.S. Pat. No. 7,288,093 to Michelson; U.S. Pat. No. 7,207,992 to Ritland; U.S. Pat. No. 7,077,864 Byrd III, et al.; U.S. Pat. No. 7,025,769 to Ferree; U.S. Pat. No. 6,719,795 to Cornwall, et al.; U.S. Pat. No. 6,364,880 to Michelson; U.S. Pat. No. 6,328,738 to Suddaby; U.S. Pat. No. 6,290,724 to Marino; U.S. Pat. No. 6,113,602 to Sand; U.S. Pat. No. 6,030,401 to Marino; U.S. Pat. No. 5,865,846 to Bryan, et al.; U.S. Pat. No. 5,569,246 to Ojima, et al.; U.S. Pat. No. 5,527,312 to Ray; and U.S. Pat. Appl. No. 2008/0255564 to Michelson.

Several advantages of an improved depth control apparatus have previously been described herein, but for convenience, the following advantages are contemplated by this disclosure: customizable apparatus for use with a specific or numerous different instruments, tools or other surgical equipment, including both motorized and non-motorized; materials that permit 3D printing or otherwise simplify the fabrication of the components of the apparatus; reusability and/or disposability of components; ease of identification, orientation and established depth/penetration of associated instruments; lockable and unlockable configurations; ease of assembly; inhibition or prohibition to rotate or "slip" once assembled; ease of adjustment to achieve different depths; pre-surgically assembled to decrease time of operation and associated exposure to radiographic or other energy-emitting equipment; ease of removal; safety in that the device will not over penetrate if it becomes loose; and ability to use alone or in conjunction with patient-specific devices as described in greater detail below.

Several views of the apparatus described herein are shown in FIGS. 1A-7B. The apparatus of the present disclosure preferably employs two primary components or portions. The first portion is referred to herein as the body portion 10 or simply "the body." The second portion is referred to herein as the collar portion 20 or simply "the collar." These two components are configured to connect in a specific manner and in combination provide a depth stop or hard stop apparatus when used in connection with a cutting instrument 30, such as a drill bit. In one embodiment, the two components 10, 20 are assembled together in a press-fit connection to form a depth stop assembly. In other embodiments, the body 10 and collar 20 portions are manufactured in a pre-assembled configuration.

The depth stop assembly preferably interfaces with at least one guide, such as a cannula. This interface permits a surgeon or other user to determine the "zero" location for a prescribed depth, vis-à-vis the at least one guide. The apparatus of the present disclosure also preferably interfaces with at least one instrument, tool or other surgical device that allows the assembly to prevent penetration of the at least one instrument, tool or other surgical device beyond a specific depth or distance. In embodiments, the instrument is a drill bit, although other cutting instruments are contemplated for use with the apparatus and are described in further detail below.

In embodiments, the body 10 and collar 20 portions may be 3D printed out of a metal or plastic (including but not limited to steel, stainless steel, metal alloys, polyurethane, polyethylene, ABS, resin-based materials, nylon or equivalent) material. In embodiments, the apparatus is intended to be single use. In other embodiments, the apparatus is reusable.

In embodiments, the depth stop assembly may lack a collar 20 portion but still interfaces with a cutting apparatus. In this embodiment, the depth stop assembly does not include a lockable configuration.

Figure 1A:
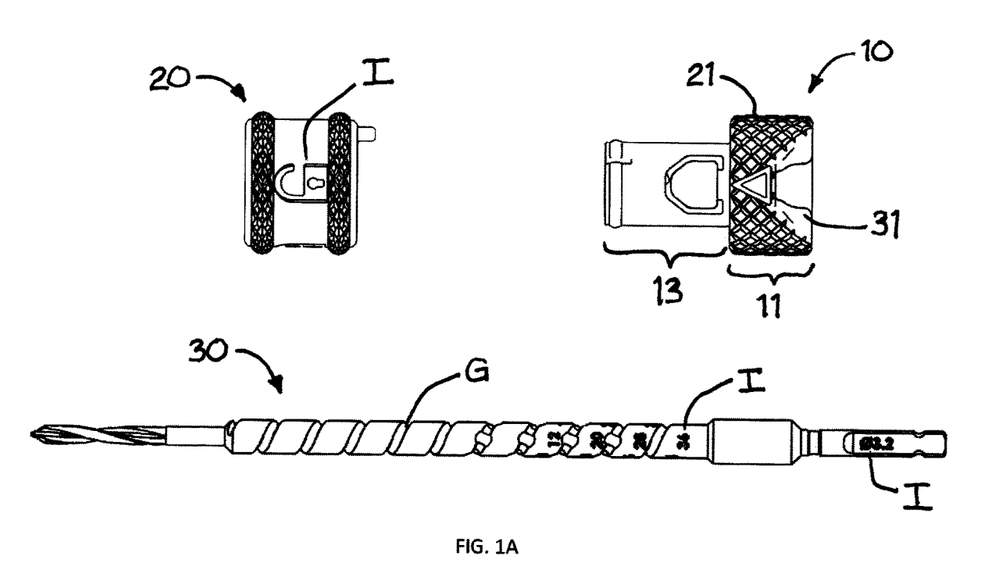
FIGS. 1A-1F show multiple views of the apparatus configured for assembly with a cutting instrument according to embodiments of the present disclosure.
Figure 1B:
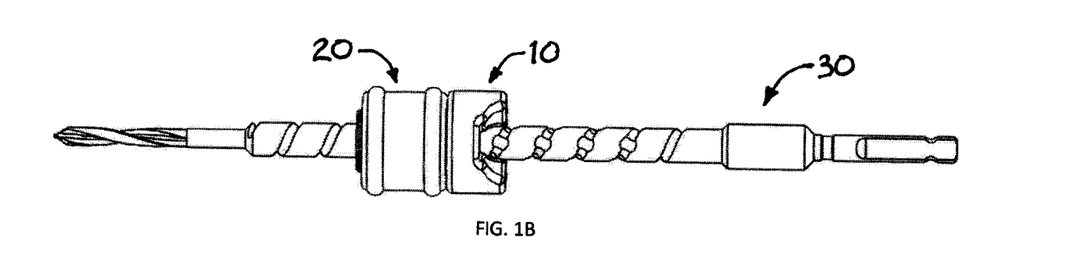
Figure 1C:
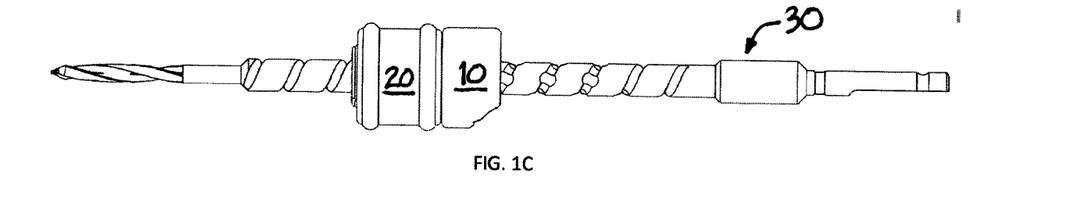
Figure 1D:
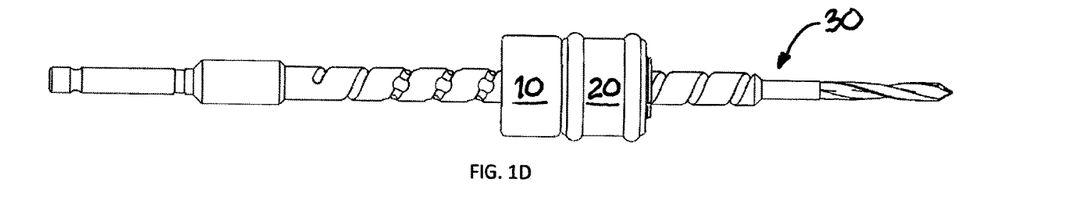
Figure 1E:
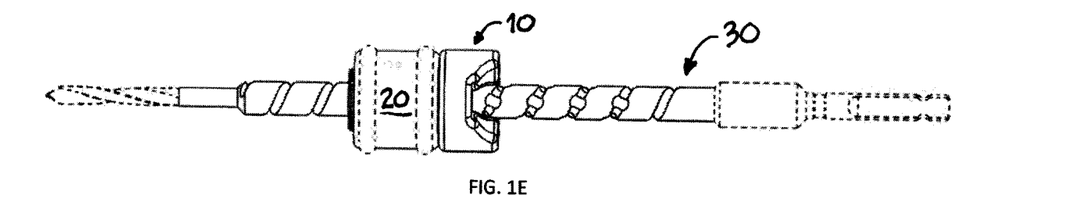
Figure 1F:
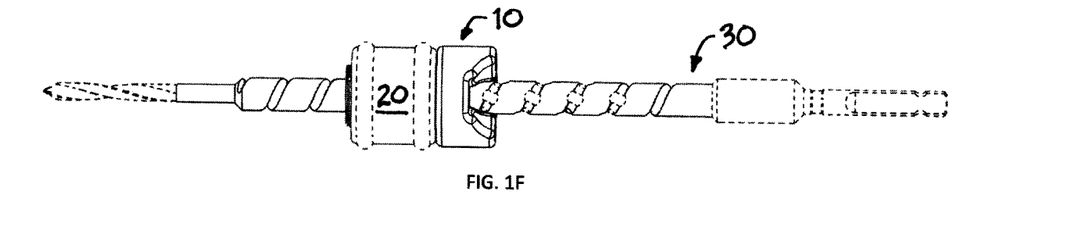
Figure 7A:
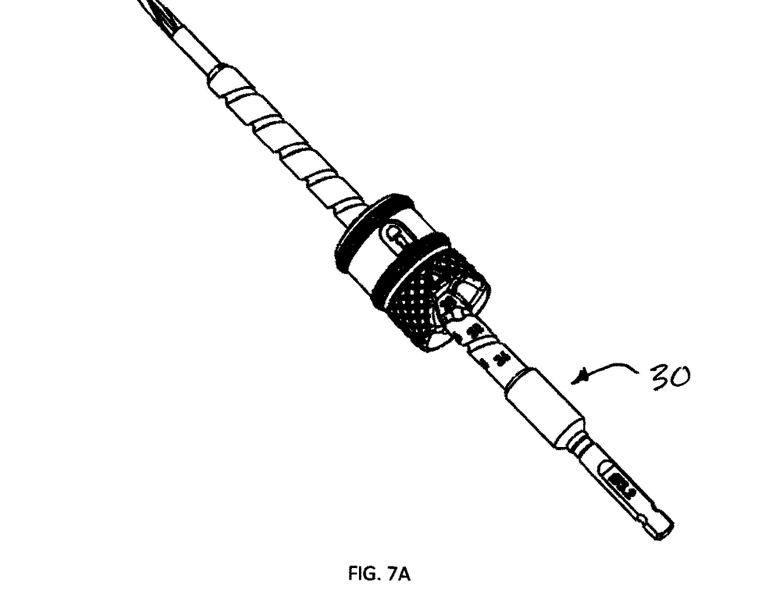
FIG. 7A shows a perspective view of the collar and body assembled with the cutting instrument of FIG. 5 according to embodiments of the present disclosure.
Figure 7B:
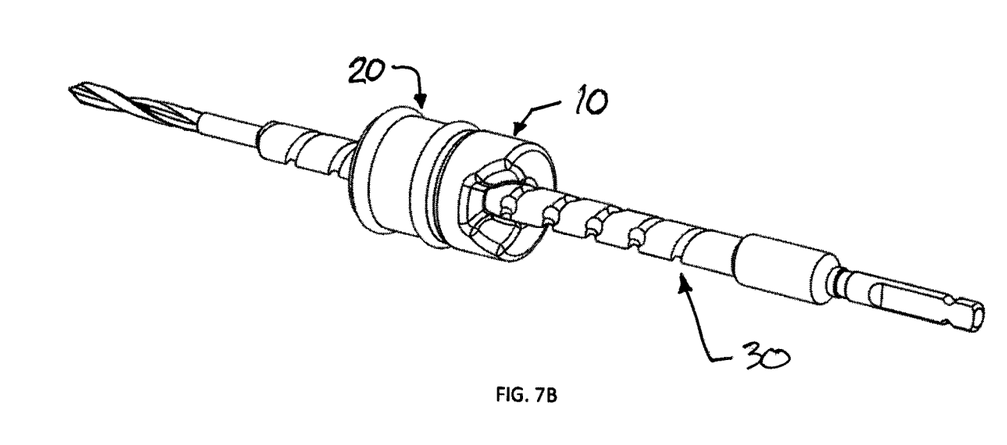
FIG. 7B shows a perspective view of the collar and body assembled with the cutting instrument of FIG. 5 according to alternate embodiments of the present disclosure.

An exploded view of the system is shown below in FIG. 1A. In this embodiment, the collar 20 preferably couples to a first section of the body 10. Then, the collar 20 and body 10 assembly (referred to herein as "the apparatus") is then coupled to the cutting instrument 30 as shown in FIGS. 7A-7B. In alternate embodiments, the body 10 is coupled to the cutting instrument 30 and then the collar 20 portion is coupled to the body 10 portion. As shown in FIG. 1A, the cutting instrument 30 may comprise a male/female groove G or channel along at least a portion of its length, and may further comprise one or more indicia I for indicating the associated depth or distance from a distal end of the cutting instrument 30, such as the sharpened tip of a drill bit, for example. FIGS. 1B-1F show multiple elevation views of body 10 and collar 20 portions in different relative positions and/or orientations when assembled with the cutting instrument 30.

Referring now to FIGS. 2A-2D, several detailed view of the body 10 of the apparatus are shown. The body 10 is preferably generally cylindrical, although variations along the length of the body 10 are contemplated and shown in FIG. 2A. In these embodiments, the body 10 may comprise a first section having a smaller outer diameter 13 and a second section having a larger outer diameter 11. The larger outer diameter section 11 is preferably used to manipulate and/or position the depth stop assembly. This section 11 also preferably comprises ergonomic features, such as a knurling 21 and/or thumb indentation 31 for improved purchase by a user's fingers and subsequent manipulation and use. The space for the thumb indentation 31 may also serve as a location of a cut-out or marking window, which permits a user to align the marking window with indicia I on the cutting instrument 30, and which notifies the user the permissible depth of the instrument 30 in conjunction with the depth stop apparatus.

Figure 2A:
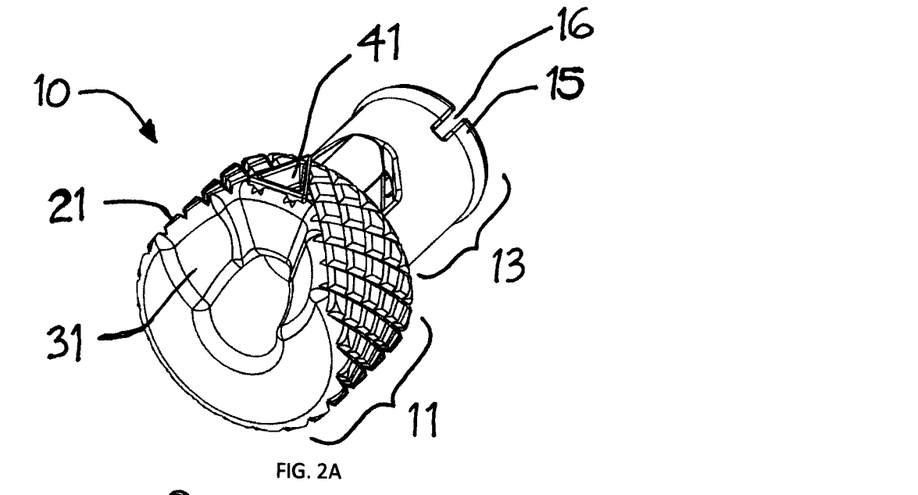
FIGS. 2A-2D show multiple views of the body of the apparatus according to embodiments of the present disclosure.

The body 10 may also comprise an orientation viewport 41, which is further used to align the body 10 portion with markings on the collar 20 portion, and/or to notify the user when the depth stop is locked or unlocked. The viewport 41 may be located and sized in a manner to prevent misreading indicia I on either the cutting instrument 30 or the collar 20 inadvertently.

The first section of the body 13 may comprise a raised ridge 15, which serves to assist with retaining the collar 20 once the components have been coupled together and the apparatus assembled. One or more relief cuts 16 may be provided along the raised ridge 15 to aid in the assembly process.

Figure 2B:
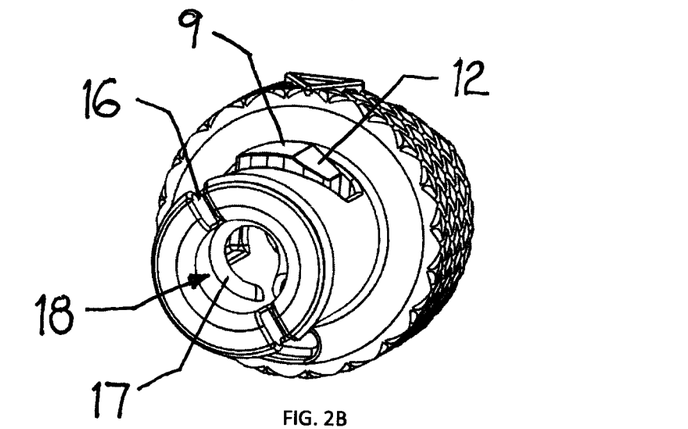

Referring now to FIG. 2B, the body 10 preferably comprises a bore or inner diameter 18 that runs through at least a portion of the first and second sections of the body. The inner diameter 18 preferably comprises internal threads 17, which match (i.e., in a male/female or female/male threaded arrangement) the thread form of the cutting instrument 30. The internal threads 17 are preferably arranged substantially or completely in a helical arrangement, which helps to keep the depth stop in the correct location, aids in controlling adjustment of depth incrementally, and prevents the apparatus from moving during use.

Figure 2C:
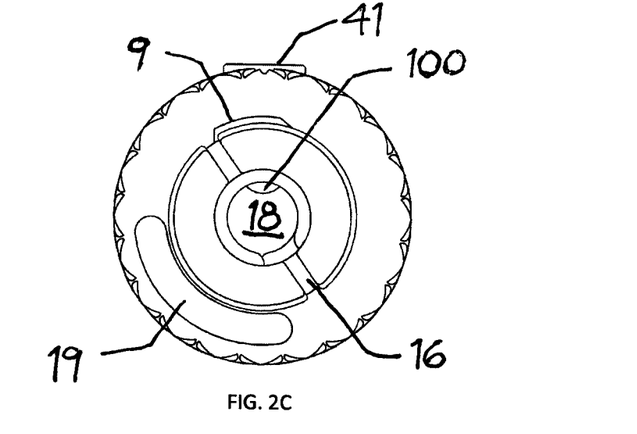
Figure 2D:
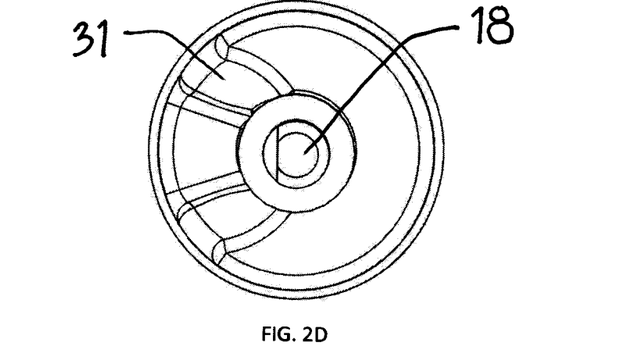

Referring to FIG. 2C, a keyway 19 is shown. This keyway 19 preferably mates with a key K on the collar 20, and which in turn controls and/or limits the rotation of the collar 20 between the locked and unlocked positions, which is described in greater detail below. The keyway 19 is sized to receive the key K on the collar 20 in a congruent manner, such that the key K is not easily displaced from the keyway 19 once the body 10 and collar 20 portions are joined together. A top plan view of the body 10 is shown in FIG. 2D.

Figure 3A:
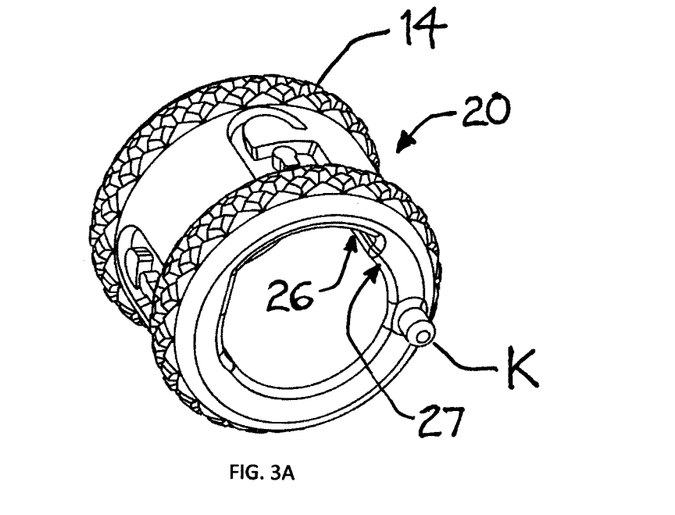
FIGS. 3A-3B show multiple views of the collar of the apparatus according to embodiments of the present disclosure.
Figure 3B:
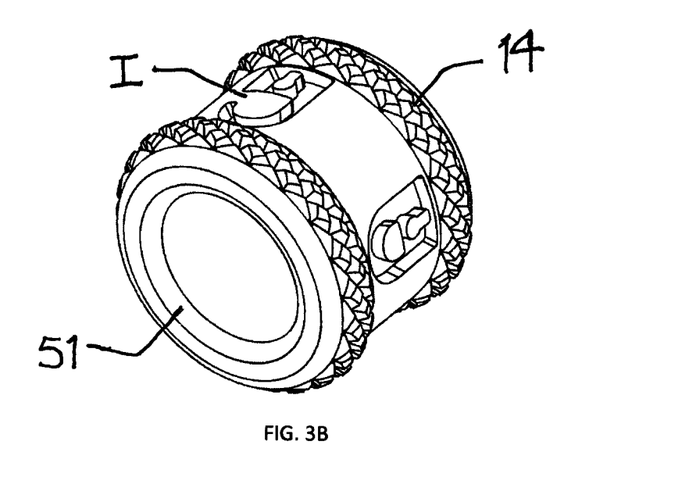

Referring now to FIGS. 3A-3B, the collar 20 portion of the apparatus is shown. Similar to the body 10, the collar 20 is preferably cylindrical (or generally cylindrical) and comprises a bore or inner diameter. The collar 20 portion preferably comprises a key K, which interfaces with the keyway 19 of the body 10 portion as described above. The collar 20 portion also preferably includes a "lock" and "unlock" graphic or other indicia I, which when positioned in line with the orientation viewport 41 of the body 10 will display to the user an "unlocked" or "locked" symbol or other indicia I corresponding to an unlocked or locked apparatus. In embodiments, the orientation viewport 41 is substantially in the shape of an arrowhead or triangle, such that the leading point of the triangle points towards the pertinent indicia I. The collar 20 also preferably comprises knurling 14, which comprise surface features raised larger than the knurling 21 on the body 10. This difference in knurling or other surface feature helps in identification of the two components by feel/touch when the apparatus is being assembled or is in use. The collar 20 preferably comprises a closed portion 51 where a ridge 15 of the body terminates once the two components are joined together.

Referring again to FIG. 2B, a tab 9 is preferably provided on the first portion 13 of the body 10, which is designed to flex up and down as it contacts a ball 100 (partially shown in FIG. 2C) situated under the tab 9. This ball 100 is also moved in and out of detents preferably formed within the groove and along the length of the cutting instrument 30, as described in greater detail below. When the collar 20 is rotated to the locked position, the tab 9 is held down which results in the ball 100 being retained in at least one detent formed along the groove of the cutting instrument 30, which locks the device. A ramp 12 on the tab 9 aids in the transition between unlocked and locked as the collar rotates.

Referring again to FIG. 3A, the collar 20 portion also comprises an open or expanded portion 26, which allows for the tab 9 of the body 10 to flex outwardly into the expanded portion 26 of the collar 20 when the collar 20 is in an unlocked position. The collar 20 also comprises a closed portion 27, which prevents the tab 9 of the body 10 to flex outward into the collar's expanded portion 26 when the collar 20 is in a locked position. A detent may be provided in the internal diameter of the collar 20 to further achieve this objective.

Figure 4A:
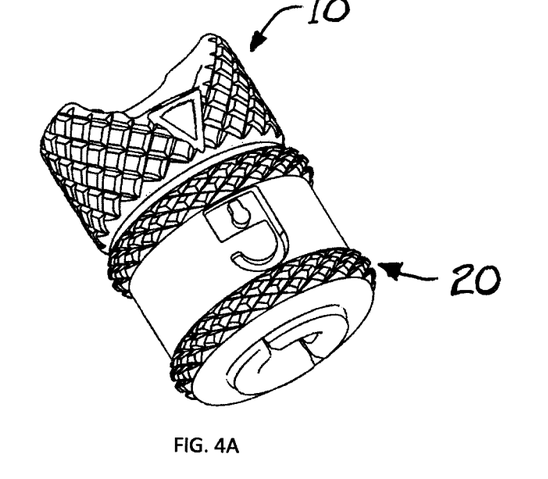
FIGS. 4A-K show multiple views of the body and collar in an assembled state according to embodiments of the present disclosure.
Figure 4B:
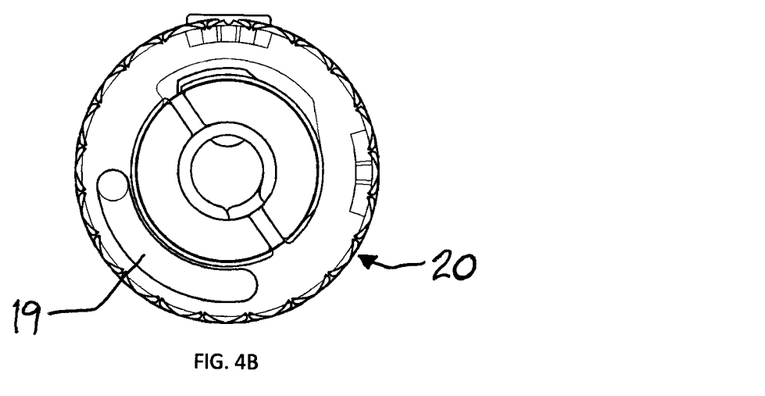
Figure 4C:
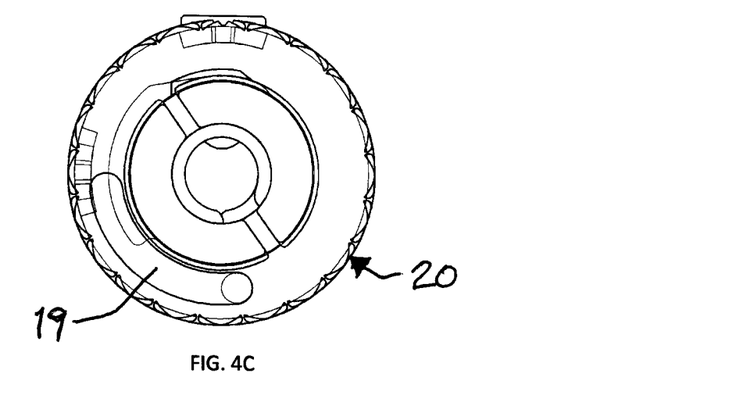
Figure 4D:
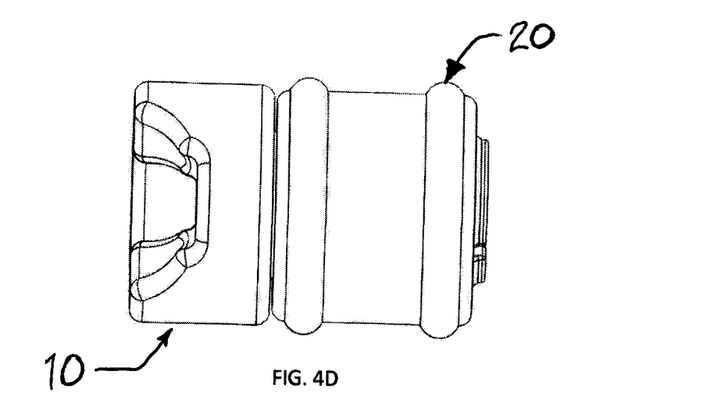
Figure 4E:
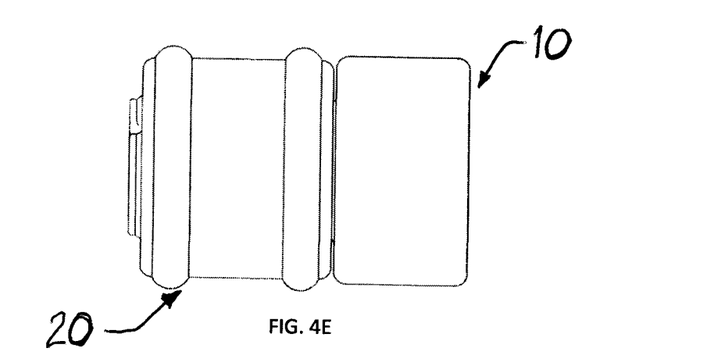
Figure 4F:
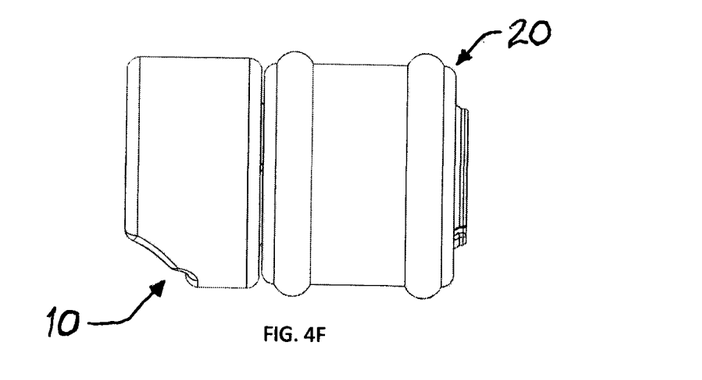
Figure 4G:
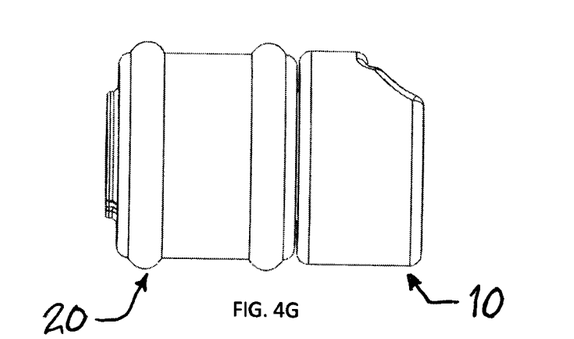
Figure 4H:
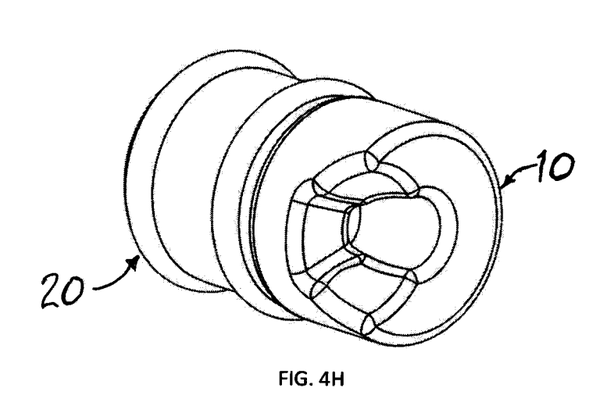
Figure 4I:
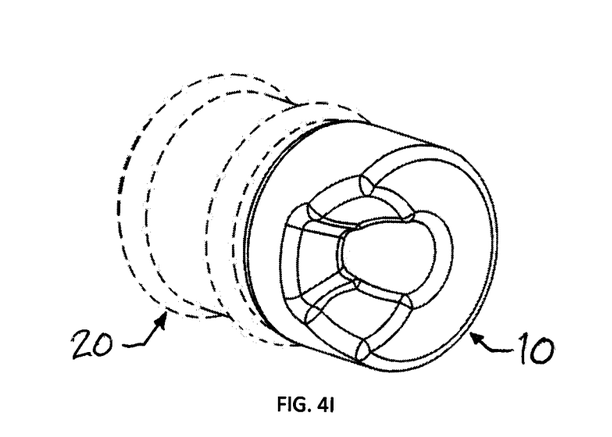
Figure 4J:
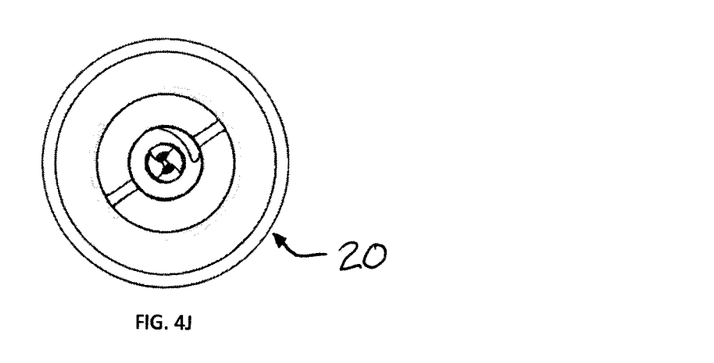
Figure 4K:
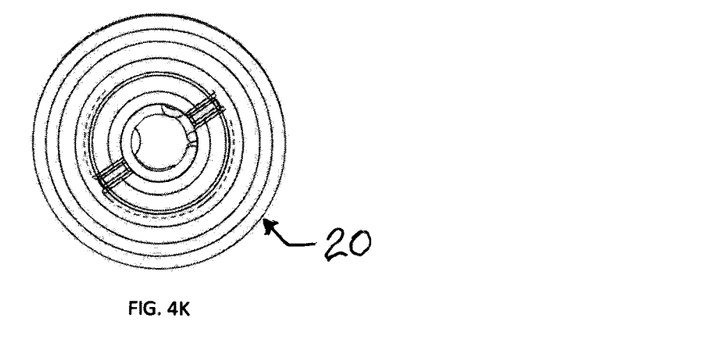

Referring to FIGS. 4A-4K, multiple views of the final assembled depth stop can be seen in the images below. These images include the locked vs. unlocked orientations of the device. FIG. 4A shows the assembled apparatus in a perspective view. FIG. 4C shows a plan view of the collar 20 portion in a locked orientation, and FIG. 4B shows a plan view of the collar 20 portion in an unlocked orientation. FIGS. 4D-4G show elevation views of the body 10 and collar 20 in an assembled configuration. FIGS. 4H-4I show perspective views of the assembled apparatus, and FIGS. 4J-4K show additional views of the assembly.

In the preferred embodiment, the collar 20 is rotated on the body 10 to achieve the locked position of the tab 9. In other embodiments, the collar 20 is slidable along the major axis of the body 10 to achieve the locked position of the tab 9. In yet other embodiments, the collar 20 is first slidable along the major axis of the body 10 and is then rotated to achieve the locked position of the tab 9.

Figure 5:
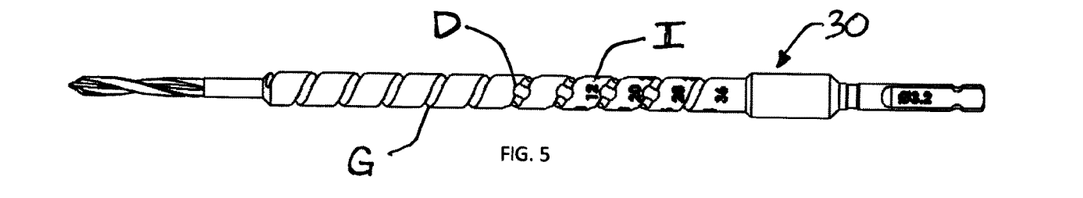
FIG. 5 shows a detailed view of a cutting instrument according to embodiments of the present disclosure.

Referring now to FIG. 5, an instrument 30 for use with the apparatus described above is shown. Here, a cutting instrument 30 preferably comprises a helical male/female groove or channel G to facilitate coupling with the apparatus and to control the depth of the depth stop apparatus. This channel G also facilitates retaining the depth stop in place, and to orient the depth stop. In a preferred embodiment, the helical grove G is the reverse direction (i.e., counterclockwise) in relation to the cutting end of the instrument 30. This allows for the drill bit to back out or reverse if the depth stop is jammed or locked up and prevents the cutting instrument 30 from plunging deeper into the patient when the cutting instrument 30 remains in the forward cutting direction. The helical grove G preferably comprises a specific pitch, such that a specific turn/rotation of the depth stop apparatus by a specific amount results in the desired drill depth increment change. In a preferred embodiment, a ¼ turn equates to a movement of 2 mm. In another embodiment the helical grove G is in the same direction in relation to the cutting end of the instrument.

The cutting instrument 30 preferably comprises a plurality of detents D along the channel or groove G, which interface with the ball 100 (and thereby the tab 9) of the body 10 portion as described above. The detents D are preferably shaped and/or contoured in a congruent manner to the spherical dimensions of ball 100.

The cutting instrument 30 preferably comprises one or more markings or indicia I, which are viewable from the marking window 41 described above for proper orientation of the depth stop to the desired depth. The indicia I are preferably orientated such that, if the depth stop is joined to the cutting instrument 30 in the reverse (i.e., improper) orientation, no markings will be visible within the marking window 41.

Figure 6:
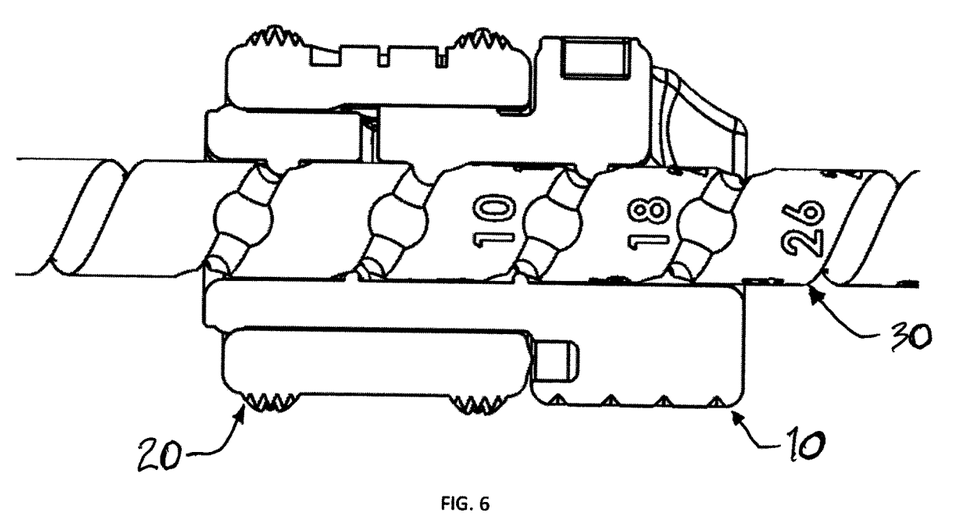
FIG. 6 shows a partial sectional view of the body and collar of the apparatus relative to a cutting instrument according to embodiments of the present disclosure.

Referring now to FIG. 6, a partial sectional view of the depth stop apparatus is shown relative to an exemplary cutting instrument 30 or tool. As can be seen in the profile of FIG. 6, the tab 9 is sunk while the ball 100 is within one of the plurality of detents D described above. Alternatively, when the ball 100 is not within one of the plurality of detents D, the tab 9 will be raised. This is permitted even when the collar 20 portion is joined to the body 10 portion, so long as the tab 9 remains in the expanded portion 26 of the inner diameter of the collar 20.

Referring to FIGS. 7A-7B, the assembly of the body portion, collar portion and cutting instrument are shown. As shown, the collar 20 is oriented relative to the body 10 to indicate a "locked" position, and the orientation viewport 41 is arranged to permit viewing of the indicia I along the length of the cutting instrument 30. The assembly according to an alternate embodiment is shown in FIG. 7B.

This assembly and apparatus provides several benefits of the prior art. For instance, the reverse orientation of the channel of the cutting instrument (in comparison to the orientation of the blade of the cutting instrument) ensures that if the connection between the apparatus and the cutting instrument becomes insecure, the effect is the cutting instrument is backed out of the guide. As another example, the apparatus may be easily coupled to multiple cutting instruments in advance of the surgery, and thereby achieve multiple cutting depths without having to remove and replace a cutting guide or hard stop to the shaft of the cutting instrument. As yet another example, the depth stop apparatus described above comprises at least two projections. The first orients the depth stop along the track of the cutting instrument, and the second constrains the depth stop from moving from its intended position and along the track of the cutting instrument. Additionally, the desired depth or distance is controlled between detents in set increments (preferably 2 mm increments), as opposed to controlling depth by visual inspection or observation of a display, or requiring a secondary source to verify the depth.

The depth control apparatus and the above-described components may be manufactured via additive manufacturing. The depth control apparatus may be used in various orthopedic surgical procedures. In one embodiment, the depth control apparatus may be used in various spinal procedures in all approaches (anterior, direct lateral, transforaminal, posterior, posterior lateral, direct lateral posterior, etc). Specific features described herein can address certain surgical objectives, for example restoring lordosis, restoring disc height, restoring sagittal or coronal balance, etc.

The apparatus described herein may then be fabricated by any method. Fabrication methods may comprise the use of a rapid prototyping machine, a 3D printing machine, a stereolithography (STL) machine, selective laser sintering (SLS) machine, or a fused deposition modeling (FDM) machine, direct metal laser sintering (DMLS), electron beam melting (EBM) machine, or other additive manufacturing machine.

According to an alternative embodiment, anatomical data may be obtained from an ultrasonic or nuclear medicine scanning device. In yet another alternative embodiment, the data may be supplemented or merged with data from a bone density scanner to fabricate a device that is designed to remain in the patient after the surgical procedure is completed, or alternatively to achieve further control over the orientation of any desired axes, particularly where the surgical procedure involves insertion of one or more implantable devices.

One having skill in the art will appreciate that embodiments of the present disclosure may have various sizes. The sizes of the various elements of embodiments of the present disclosure may be sized based on various factors including, for example, the anatomy of the patient, the person or other device operating with or otherwise using the apparatus, the surgical site location, physical features of the devices and instruments used with the apparatus described herein, including, for example, width, length and thickness, and the size of the surgical apparatus.

One having skill in the art will appreciate that embodiments of the present disclosure may be constructed of materials known to provide, or predictably manufactured to provide the various aspects of the present disclosure. These materials may include, for example, stainless steel, titanium alloy, aluminum alloy, chromium alloy, and other metals or metal alloys. These materials may also include, for example, PEEK, carbon fiber, ABS plastic, polyurethane, polyethylene, photo-polymers, resins, particularly fiber-encased resinous materials rubber, latex, synthetic rubber, synthetic materials, polymers, and natural materials.

One having skill in the art will appreciate that embodiments of the present disclosure may be used in conjunction devices that employ automated or semi-automated manipulation. Various apparatus and implants described herein may be provided to facilitate or control the entry point, angular trajectory, height, and/or head orientation of a screw, for example. For example, the drill may include further attachments to use with taps, burrs, trials or other surgical tools and instruments.

Additional benefits of the systems and methods described herein include improving device fixation, and/or preventing unwanted contact between devices and patient anatomy (e.g. the patient's spinal cord). The further use of methods described above, including the use of software analytics, may further aid in determining screw placement and orientation to achieve the ideal screw placement and/or rod shape. For example, the use of various apparatus described herein to achieve desired screw placement and orientation in turn provides improved alignment of a secondary device, such as a rod, with the screws heads. This benefit in turn allows the surgeon/user to achieve optimal sagittal and/or coronal alignment, which assists in rod placement and improves correction of the patient's anatomy.

While various embodiments of the present disclosure have been described in detail, it is apparent that modifications and alterations of those embodiments will occur to those skilled in the art. However, it is to be expressly understood that such modifications and alterations are within the scope and spirit of the present disclosure. For further illustration, the materials provided in the provisional patent application from which this application claims priority to, including Appendix A thereto, are expressly made a part of this disclosure and incorporated by reference herein in their entirety.

It is expressly understood that where the term "patient" has been used to describe the various embodiments of the disclosure, the term should not be construed as limiting in any way. For instance, a patient could be either a human patient or an animal patient, and the apparatus and methods described herein apply equally to veterinary science as they would to surgical procedures performed on human anatomy. The apparatus and methods described herein therefore have application beyond surgical procedures used by spinal surgeons, and the concepts may be applied to other types of "patients" and procedures without departing from the spirit of the present disclosure.

The foregoing discussion of the disclosure has been presented for purposes of illustration and description. The foregoing is not intended to limit the disclosure to the form or forms disclosed herein. In the foregoing Detailed Description for example, various features of the disclosure are grouped together in one or more embodiments for the purpose of streamlining the disclosure. This method of disclosure is not to be interpreted as reflecting an intention that the claimed disclosure requires more features than are expressly recited in each claim. Rather, the inventive aspects lie in less than all features of a single foregoing disclosed embodiment.

The present inventions, in various embodiments, include components, methods, processes, systems and/or apparatuses substantially as depicted and described herein, including various embodiments, subcombinations, and subsets thereof. Those of skill in the art will understand how to make and use the present inventions after understanding the present disclosure. The present inventions, in various embodiments, include providing devices and processes in the absence of items not depicted and/or described herein or in various embodiments hereof, including in the absence of such items as may have been used in previous devices or processes, e.g., for improving performance, achieving ease and/or reducing cost of implementation.

Moreover, though the present disclosure has included description of one or more embodiments and certain variations and modifications, other variations and modifications are within the scope of the disclosure, e.g., as may be within the skill and knowledge of those in the art, after understanding the present disclosure. It is intended to obtain rights which include alternative embodiments to the extent permitted, including alternate, interchangeable and/or equivalent structures, functions, ranges or steps to those claimed, whether or not such alternate, interchangeable and/or equivalent structures, functions, ranges or steps are disclosed herein, and without intending to publicly dedicate any patentable subject matter.

What is claimed is:

1. An apparatus configurable to contact and be secured to an instrument, the apparatus comprising:
    a cylindrical body comprising at least a first portion and a second portion, the first portion having a smaller radial dimension than the second portion, the cylindrical body further comprising a longitudinal axis through a radius of the cylindrical body, the cylindrical body further comprising a bore passing through the cylindrical body and about the longitudinal axis of the cylindrical body for receiving at least a certain length of the instrument, wherein the bore comprises at least one track for engaging at least a portion of the instrument; and
    a collar comprising a bore and selectively engageable with the cylindrical body by placement of the first portion of the cylindrical body in the bore of the collar, the bore comprising at least one first section having a first radial dimension and a second expanded section having a second radial dimension greater than the first radial dimension, the bore further comprising at least one detent that is selectively engageable with the instrument.

2. The apparatus of claim 1 wherein the collar comprises a projection substantially parallel to the collar's longitudinal axis and selectively positionable within a slot formed in a surface of the second portion of the body, the projection capable of moving within the slot upon rotation of the collar relative to the body.

3. The apparatus of claim 2, wherein the first portion of the body further comprises at least one tab configured to be displaced radially when the collar is engaged with the first portion of the body and rotated, the displacement of the tab resulting in further contact with the instrument, wherein the expanded section of the bore of the collar is configured to receive the tab without displacing the tab in a first position of use, wherein the first position of use maintains the apparatus in an unlocked position, and wherein the collar may be rotated to cause displacement of the tab in a second position of use which maintains the apparatus in a locked position of use.

4. The apparatus of claim 3 further comprising at least two projections, wherein a first projection is configured to contact the instrument and orient the body along a groove formed in an outer circumference of the instrument, and wherein a second projection secures the apparatus in a desired position relative to the instrument.

5. The apparatus of claim 4 wherein the first projection is formed along the bore of the body and is arranged in a substantially helical shape, and wherein the first projection is configured to be placed within the groove formed in the outer circumference of the instrument.

6. The apparatus of claim 5 wherein the second projection is associated with the tab.

7. The apparatus of claim 5 wherein the groove is oriented in an opposing direction to the orientation of blades associated with the instrument.

8. The apparatus of claim 5 wherein the groove of the cutting instrument comprises intermittent detents along the groove, and wherein the detents are shaped in a manner to receive the ball when the apparatus is in a second or locked position of use.

9. The apparatus of claim 1 wherein the instrument is a drill bit, a bur, a tap, a probe, a reamer, or an implant.

10. The apparatus of claim 1 wherein a specified rotation of the apparatus relative to the instrument relates to a specified translational movement of the instrument.

11. The apparatus of claim 10 wherein the specified rotation is 90 degrees to 180 degrees and the specified translational movement is in the range of 2 mm to 10 mm.

12. The apparatus of claim 1 wherein the collar further comprises a plurality of indicia, including a first indicia representing a locked position of the apparatus and a second indicia representing an unlocked position of the apparatus.

13. The apparatus of claim 1 wherein the body further comprises at least one window for observing indicia beneath the body, including indicia present on the instrument.

14. The apparatus of claim 1 wherein the cylindrical body further comprises a marker for visually identifying a position of the collar relative to the cylindrical body in either a locked or unlocked position of use.

15. The apparatus of claim 1 wherein at least a portion of the body or the collar further comprises surface texturing for improving manipulation of the cylindrical body or the collar.

16. The apparatus of claim 1 wherein the cylindrical body and collar are formed of a stainless steel, a titanium alloy, an aluminum alloy, a chromium alloy, a metal alloy, a PEEK material, a carbon fiber, an ABS plastic, a polyurethane, a polyethylene, a photo-polymer, a resin, a fiber-encased resinous material, a rubber material, a latex material, a synthetic rubber, a synthetic material, a polymer, or a natural material.

17. An apparatus configurable to contact and be secured to an instrument, the apparatus comprising:
- a body comprising at least a first portion and a second portion, the first portion having a smaller radial dimension than the second portion, the body further comprising a central axis and a bore passing through the central axis of the body for receiving at least a certain length of the instrument;
- a cylindrical, hollow collar selectively engageable with the body by placement of the at least a first portion of the body in a hollow portion of the collar, wherein the hollow portion of the cylindrical, hollow collar comprises at least one first section having a radial dimension greater than second section of the hollow portion of the collar;
- the cylindrical, hollow collar comprising a projection substantially parallel to the cylindrical, hollow collar's longitudinal axis and selectively positionable within a slot formed in a surface of the second portion of the body, the projection capable of moving within the slot upon rotation of the cylindrical, hollow collar relative to the body;
- the first portion of the body further comprising at least one tab configured to be displaced radially when the cylindrical, hollow collar is engaged with the first portion of the body and rotated, the displacement of the tab resulting in further contact with the instrument;
- wherein the at least one first section of the hollow portion of the collar is configured to receive the tab without displacing the tab in a first position of use, wherein the first position of use maintains the apparatus in an unlocked position, and wherein the cylindrical, hollow collar may be rotated to cause displacement of the tab in a second position of use which maintains the apparatus in a locked position of use.

18. The apparatus of claim 17 further comprising at least two projections, wherein a first projection is configured to contact the instrument and orient the body, and wherein a second projection secures the apparatus in a desired position relative to the instrument.

19. The apparatus of claim 18 wherein the first projection is formed along the bore of the body and is arranged in a substantially helical shape, and wherein the first projection is configured to be placed within the groove formed in the outer circumference of the instrument.

* * * * *